(12) United States Patent
Koh

(10) Patent No.: US 8,175,704 B2
(45) Date of Patent: May 8, 2012

(54) TECHNIQUES FOR DELIVERY OF STEM CELL AND RELATED THERAPIES TO TREAT CARDIAC CONDITIONS

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 12/841,913

(22) Filed: Jul. 22, 2010

(65) Prior Publication Data

US 2010/0286652 A1 Nov. 11, 2010

Related U.S. Application Data

(62) Division of application No. 11/556,631, filed on Nov. 3, 2006, now Pat. No. 7,787,950.

(51) Int. Cl.
*A61N 1/362* (2006.01)

(52) U.S. Cl. .......................................................... 607/9

(58) Field of Classification Search .................. 607/3, 6, 607/120; 600/510; 604/890.1
See application file for complete search history.

(56) References Cited

U.S. PATENT DOCUMENTS

| | | | |
|---|---|---|---|
| 4,716,888 A * | 1/1988 | Wesner | 607/126 |
| 5,203,326 A | 4/1993 | Collins | |
| 5,571,144 A | 11/1996 | Schroeppel | |
| 5,601,615 A | 2/1997 | Markowitz et al. | |
| 5,861,013 A | 1/1999 | Peck et al. | |
| 5,871,512 A | 2/1999 | Hemming et al. | |
| 6,067,988 A | 5/2000 | Mueller | |
| 6,151,525 A | 11/2000 | Soykan et al. | |
| 6,224,566 B1 * | 5/2001 | Loeb | 604/22 |
| 6,450,172 B1 * | 9/2002 | Hartlaub et al. | 128/899 |
| 6,496,730 B1 | 12/2002 | Kleckner et al. | |
| 6,553,259 B2 | 4/2003 | Mouchawar et al. | |
| 6,671,558 B1 | 12/2003 | Soykan et al. | |
| 6,678,558 B1 | 1/2004 | Dimmer et al. | |
| 6,775,574 B1 | 8/2004 | Soykan et al. | |
| 7,031,775 B2 | 4/2006 | Soykan et al. | |
| 2001/0023346 A1 | 9/2001 | Loeb | |
| 2002/0133203 A1 | 9/2002 | Mouchawar et al. | |
| 2003/0004548 A1 | 1/2003 | Warkentin | |
| 2003/0014010 A1 * | 1/2003 | Carpenter et al. | 604/117 |
| 2003/0074029 A1 | 4/2003 | Deno et al. | |
| 2004/0093034 A1 * | 5/2004 | Girouard et al. | 607/3 |

(Continued)

FOREIGN PATENT DOCUMENTS

WO 0220088 A1 3/2002

(Continued)

OTHER PUBLICATIONS

Baar, Keith et al., "Self-organization of rat cardiac cells into contractile 3-D cardiac tissue," The FASEB Journal; http://www.fasebj.org/cgi/doi/10.1096/fj.04-2034fje; doi: 10.1096/fj.04-2034fje.

(Continued)

*Primary Examiner* — Niketa Patel
*Assistant Examiner* — Hiba El-Kaissi

(57) ABSTRACT

An exemplary method includes acquiring cardiac electrical activity information; detecting cardiac events within the information including T waves, QRS complexes and/or P waves; and calling for delivery of matter to the heart during a period of time based on the cardiac events. The delivery may occur between a detected T wave and its immediately subsequent QRS complex. The matter being delivered may include stem cells, progenitor cells, nutrients and/or drugs.

14 Claims, 11 Drawing Sheets

U.S. PATENT DOCUMENTS

| | | |
|---|---|---|
| 2004/0098075 A1* | 5/2004 | Lee .................... 607/122 |
| 2004/0158289 A1 | 8/2004 | Girouard et al. |
| 2004/0158290 A1 | 8/2004 | Girouard et al. |
| 2004/0253209 A1 | 12/2004 | Soykan et al. |
| 2005/0002912 A1 | 1/2005 | Chachques |
| 2005/0043766 A1* | 2/2005 | Soykan et al. ............ 607/9 |
| 2005/0090875 A1* | 4/2005 | Palanker et al. ......... 607/54 |
| 2005/0288721 A1 | 12/2005 | Girouard et al. |
| 2006/0095089 A1 | 5/2006 | Soykan et al. |
| 2006/0136001 A1* | 6/2006 | Ortega et al. ............ 607/9 |

FOREIGN PATENT DOCUMENTS

| | | |
|---|---|---|
| WO | 03064637 A1 | 8/2003 |
| WO | 2004050180 A2 | 6/2004 |
| WO | 2004050180 A3 | 11/2004 |
| WO | 2005007233 A2 | 1/2005 |
| WO | 2005118062 A2 | 12/2005 |
| WO | 2005120635 A1 | 12/2005 |
| WO | 2005118062 A3 | 4/2007 |
| WO | 2005007233 A3 | 12/2008 |

OTHER PUBLICATIONS

Restriction Requirement, mailed Jul. 24, 2008—Parent U.S. Appl. No. 11/556,631.
NonFinal Office Action, mailed Apr. 30, 2009—Parent U.S. Appl. No. 11/556,631.
Final Office Action, mailed Jan. 8, 2010—Parent U.S. Appl. No. 11/556,631.
Notice of Allowance, mailed Jun. 15, 2010—Parent U.S. Appl. No. 11/556,631.
NonFinal Office Action, mailed Dec. 23, 2010—Related U.S. Appl. No. 12/841,931.
NonFinal Office Action, mailed Dec. 27, 2010—Related U.S. Appl. No. 12/841,944.

* cited by examiner

US 8,175,704 B2

TECHNIQUES FOR DELIVERY OF STEM CELL AND RELATED THERAPIES TO TREAT CARDIAC CONDITIONS

CROSS REFERENCE TO RELATED APPLICATIONS

This application is a division of U.S. patent application Ser. No. 11/556,631, filed Nov. 3, 2006, titled "Techniques for Delivery of Stem Cell and Related Therapies to Treat Cardiac Conditions", now U.S. Pat. No. 7,787,950 and is related to U.S. patent application Ser. No. 12/841,931, filed Jul. 22, 2010, titled "Techniques for Delivery of Stem Cell and Related Therapies to Treat Cardiac Conditions" and U.S. patent application Ser. No. 12/841,944, filed Jul. 22, 2010, titled "Techniques for Delivery of Stem Cell and Related Therapies to Treat Cardiac Conditions."

TECHNICAL FIELD

Subject matter presented herein relates generally to stem cell and related therapies. More specifically, various techniques pertain to use of cardiac electrical activity and other physiological information to enhance such therapies.

BACKGROUND

Various studies report use of stem cell and related therapies for improving cardiac performance. Proposed mechanisms include passive effects on scar tissue, neovascularization leading to reduced cardiomyocyte apoptosis, cell fusion and paracrine effects leading to proliferation of endogenous cardiomyocytes and cardiomyocyte regeneration as well as transdifferentiation leading to cardiomyocyte regeneration. While some view a lack of understanding as to specific mechanisms by which stem cell and related therapies improve cardiac performance, various processes have nevertheless been identified as being beneficial to such therapies. For example, many therapies include processes such as conditioning cells with electrical stimuli, injecting cells into the body, feeding cells, etc. With respect to applying electrical stimuli, various studies indicate that such conditioning can reduce myocardial heterogeneity (e.g., electrical and/or structural), which may cause paroxysmal arrhythmia.

Some studies advocate in vivo conditioning while others report that in vivo conditioning is not required. For example, a study by Yang et al., "Rapid stimulation causes electrical remodeling in cultured atrial myocytes", *J Mol Cell Cardiol.* 2005 February; 38(2):299-308, reported that rapid stimulation of atrial cells in culture produces electrical remodeling and that in vivo conditions are not required for the development of electrical remodeling. Another study by Park, "Electrical stimulation enhances the expression of cardiac properties in 3-D cultured cells", reported that application of electrical stimulation during cell culture in three-dimensional scaffolds enhanced both the cardiac differentiation of mesenchymal stem cells and the functional assembly of cardiomyocytes into contractile tissue constructs.

Various exemplary technologies described herein pertain to stem cell and related therapies. For example, various technologies may mimic or reproduce biological conditions and/or mimic or reproduce therapeutic conditions to enhance stem cell or related therapies.

SUMMARY

An exemplary method includes acquiring cardiac electrical activity information, detecting a T wave and, based on the detecting, calling for delivery of matter to the heart where the matter may include one or more of stem cells, progenitor cells, nutrients and drugs. Another exemplary method includes calling for delivery of electrical energy to cells destined for implantation in the body or cells already implanted in the body. Such delivery may be timed according to cardiac electrical activity and/or delivered at an energy level below a capture threshold of neighboring tissue. Various other exemplary technologies are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
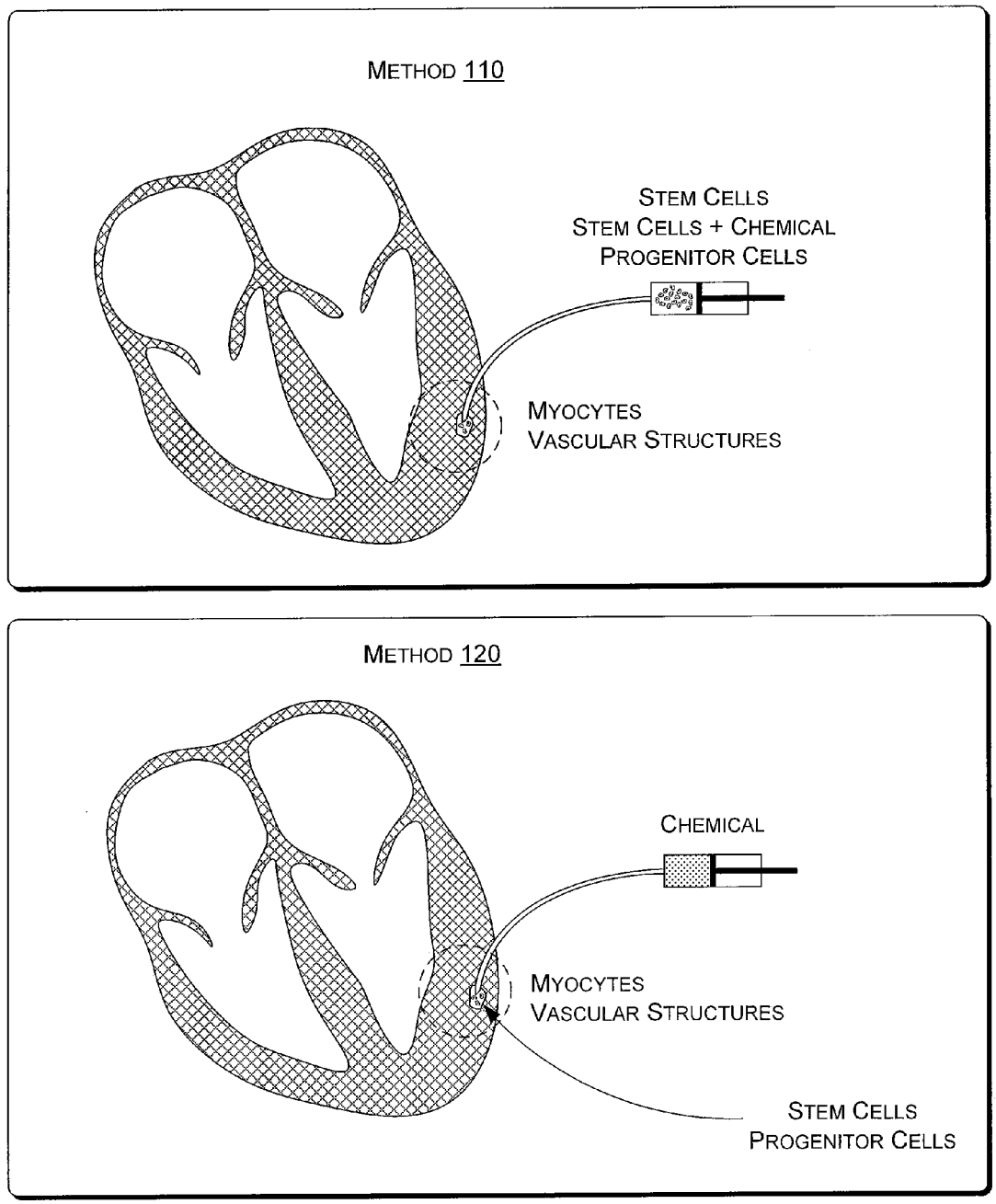
FIG. 1 is a diagram of two convention methods for treating the heart using stem cells or progenitor cells.

FIG. 1 shows two methods 110, 120 of treating a damaged region of the heart. The method 110 involves injection of cells to the heart. In this example, the cells may be stem cells, stem cells plus one or more chemicals or progenitor cells. Stem cells have both the capacity to self-renew (make more stem cells by cell division) as well as to differentiate into mature, specialized cells. A progenitor cell is an early descendant of a stem cell that can only differentiate, but it cannot renew itself anymore. In contrast, a stem cell can renew itself (make more stem cells by cell division) or it can differentiate (divide and with each cell division evolve more and more into different types of cells). A progenitor cell is often more limited in the kinds of cells it can become than a stem cell and hence more differentiated than a stem cell. Addition of a chemical to a stem cell may generate a progenitor cell.

The method 120 involves injection of one or more chemicals to the heart. The chemical(s) may act to generate progenitor cells or otherwise generate myocytes and/or vascular structures.

Whether repair occurs via injection of cells or via injection of one or more chemicals, cells or generated cells must be integrated into the heart and "learn" to function properly. Cardiac cells that beat in a cell culture, for example, may not beat in rhythm with a patient's own heart cells. And neurons injected into a damaged neural pathway must become "wired" into the pathway's intricate network of cells to connect and work properly. Further, tissue rejection should be avoided. Just as in organ transplants, immune cells may recognize transplanted cells as foreign and set off an immune reaction. Cell recipients may be advised to use of drugs to at least temporarily suppress their immune systems.

Figure 2:
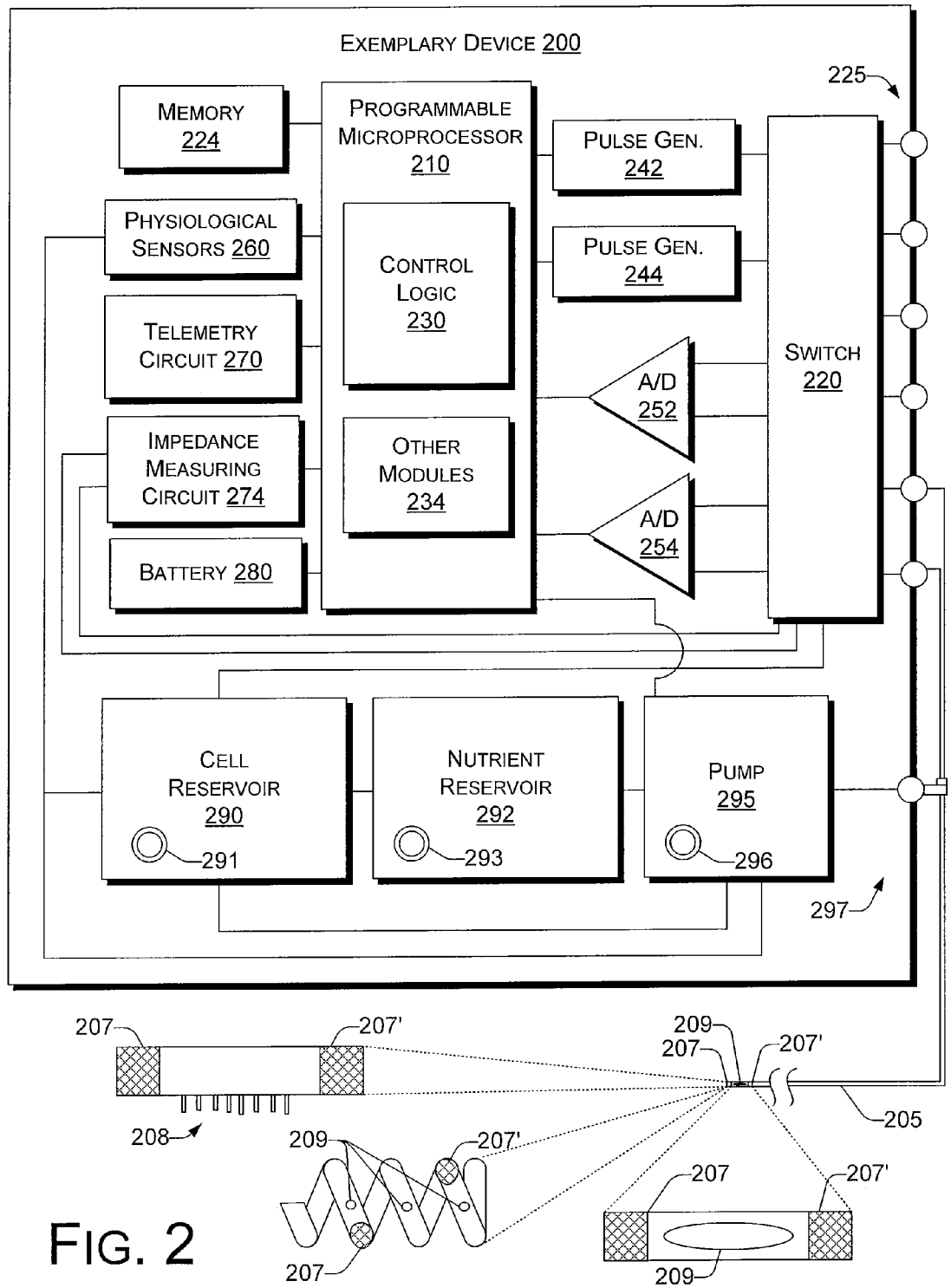
FIG. 2 is a diagram of an exemplary device and various exemplary leads for use in stem cell or related therapies.

FIG. 2 shows a block diagram of an exemplary device capable of performing any of a variety of actions including actions of the method 110 and the method 120. A basic device may include a processor, memory, one or more inputs, one or more outputs and control logic stored as instructions in the memory and operable in conjunction with the processor. The device 200 includes various additional features.

The exemplary device 200 includes a programmable microprocessor 210 that can implement control logic 230 and other instructional modules 234. Information may be stored in memory 224 and accessed by the programmable microprocessor 210. For delivery of electrical energy, the device 200 includes one or more pulse generators 242, 244. The pulse generators 242, 244 may rely on a switch 220 for delivery of energy via one or more connectors 225. While a device may include one or more integral leads, in general, a device includes one or more connectors for connecting a lead or leads to the device. More particularly, the connectors 225 provide for electrically connecting one or more electrodes to the circuitry of the device 200. In the example of FIG. 2, the switch 220 may select an appropriate electrode configuration. An electrode configuration may include an electrode from one lead and an electrode from another lead, a case electrode and another electrode or electrodes from a single lead.

The device 200 further includes one or more analog to digital converters 252, 254 for converting analog signals to digital signals or values. The processor 210 may use a signal provided by one of the ND converters 252, 254 to control a therapy or other process. A control signal from the processor 210 may instruct the switch 220 to select a particular electrode configuration for sensing electrical or other activity. As discussed below, various techniques include sensing nerve activity or other activity.

The device may include one or more physiological sensors 260. Such sensors may be housed within a case of the device 200 (e.g., a motion sensor), include a surface mounted component, include a lead, include a remote sensor, etc. A sensor may provide a digital signal or an analog signal for use by the processor 210 or other circuitry of the device 200. A physiological sensor may provide a signal via one or more of the connectors 225.

For purposes of communication with external or other implantable devices, the device 200 includes a telemetry circuit 270. The telemetry circuit 270 may include one or more antennae for transmission and/or receipt of electromagnetic signals. Such a circuit may operate according to a specialized frequency or frequencies designated for medical devices. Various conventional implantable devices rely on an associated programmer, which is an typically an external computing device with a communication circuit suitable for communicating with an implantable device for purposes of data transfer, status checks, software download, etc. Where the circuit 270 communicates with an implantable device or a device in electrical connection with a patient's body, then the body may be a conductive medium for transfer of information. For example, the circuit 270 may be capable of communication with a specialized wristwatch where the body is relied upon as a conductor.

The device 200 further includes an impedance measuring circuit 274. Such a circuit may rely on instructions from the processor 210. For example, the processor 210 may instruct the circuit 274 to provide a measured impedance for a particular electrode configuration. In such an example, the processor 210 may also instruct the switch 220 to provide the circuit 274 with a particular electrode configuration. Impedance information may be used by the processor 210 for any of a variety of purposes. The processor 210 may store impedance or other information to memory 224 for later use or for transmission via the telemetry circuit 270.

The device 200 includes a power source, which is shown as a batter 280 in the example of FIG. 2. The battery 280 powers the processor 210 and optionally other circuitry, as appropriate. In general, the battery 280 provides power to the pulse generators 242, 244. Consequently, the battery 280 provides for operation of circuitry for processing control logic, etc., and provides for energy to activate tissue. A lead-based sensor may connect to the device 200 via one or more of the connectors 225 and be powered by the battery 280. The battery 280 may be rechargeable, replaceable, etc.

The device 200 includes a cell reservoir 290 and an associated access port 291, which may allow for insertion of a needle or other instrument. Where the device 200 is an implantable device, the port 291 may allow for transdermal access to the reservoir 290. A nutrient reservoir 292 includes an associated access port 292, which may similarly for access to the nutrient reservoir 292. A pump 295 may also include an access port 296. For example, injection of a chemical into the port may allow the pump 295 to pump the chemical to one or more locations.

The cell reservoir 290 may include cells attached to and/or contained within a cell carrier. For example, microspheres may be used to carrier cells. Such microspheres may degrade in the body and may provide nutrients for cell growth and/or chemicals for cell action (e.g., differentiation of stem cells).

The device 200 further includes a connector 297 for connecting a conduit or lead 205. In the example of FIG. 2, the lead 205 includes two electrodes 207, 207' disposed adjacent an opening 209. The opening 209 connects to the pump 295 via the connector 297. Instructions from the processor 210 may cause the pump 295 to pump matter to and/or from the cell reservoir 290 and/or the nutrient reservoir 292. In an alternative, matter may be introduced or removed via the port 296. For example, the pump 295 may operate to sample fluid via the opening 209, which may then be extracted from the device 200 via the port 296. Where the device 200 is an implantable device, the arrangement may allow sampling of fluid and/or tissue from the body of a patient. In an alternative arrangement, the lead 205 includes prongs 208 disposed between a pair of electrodes 207, 207'. The prongs 208 may anchor or help anchor the lead to tissue and allow for delivery of matter at one or more depths. In another alternative arrangement, the lead 205 includes a screw end that includes two or more electrodes 207, 207' and openings 209, for example, opening outwardly for delivery of matter (e.g., fluid, nutrients, drugs, cells, etc.).

As described in more detail below, the electrodes 207, 207' may be used for any of a variety of purposes. For example, the electrodes 207, 207' may allow for sensing cardiac electrical activity, measuring impedance, delivery of stimulation energy, generation of an electro-magnetic field, etc. Where the electrodes 207, 207' allow for sensing cardiac electrical activity, the device 200 may act based on such information by conditioning cells, pumping cells, etc. Where the electrodes 207, 207' allow for measurement of impedance, the device 200 may act on such information by deciding if matter delivered via the lead 205 is in contact with the electrodes, by deciding if the opening(s) 208 or 209 are in a particular region (e.g., tissue, fluid, etc.), by deciding if fouling has occurred of the opening(s) 208 or 209, etc. Where the electrodes 207, 207' allow for generation of an electro-magnetic field, the device 200 may generate such a field to enhance delivery of matter (e.g., cells, nutrients, drugs, etc.).

While a single lead is shown in FIG. 2, multiple leads may be used or one or more leads configured differently than the lead 205. For example, a lead may connect to a patch where the patch affixes to the heart (e.g., a wall of the left ventricle). The patch may serve as a delivery mechanism for nutrients or drugs, may serve as a reservoir for cells, may include openings for delivery of cells and may include one or more electrodes for any of a variety of purposes.

With respect to flow channels or conduits of the device 200, microfluidic technologies may be employed. Microfluidic technologies generally include one or more channels with at least one dimension of less than about a few millimeters. Microfluidic technologies may transport whole blood samples, bacterial cell suspensions, protein or antibody solutions, buffers, etc. Measurements of molecular diffusion coefficients, fluid viscosity, pH, enzyme reaction kinetics, etc., may be facilitated via microfluidic technologies. Other applications in microfluidics include capillary electrophoresis, isoelectric focusing, immunoassays, flow cytometry, cell manipulation, cell separation, cell patterning, chemical gradient formation, etc. Many applications have utility for clinical diagnostics.

With respect to pumping of matter, any of a variety of techniques may be used. For example, a pressure source (e.g., piezoelectric, mechanical, compressed gas, chemical, etc.), a mechanical pump, electrokinetic mechanisms, osmotic, electro-osmotic, etc., may be used. An exemplary device may use variations in pressure (e.g., intrapleural, intrathoracic, airway, etc.) that accompany respiration to promote flow or for pumping. For example, as the diaphragm contracts, the ribcage expands, which causes a decrease in intrathoracic pressure and flow of air into the lungs. With respect to intrapleural pressure, under normal conditions, it is always negative. The negative pressure between the two pleurae maintains partial lung expansion by keeping the lung pulled up against the chest wall. The degree of negativity, however, changes during respiration. During inhalation, the pressure is approximately −8 cm $H_2O$; during exhalation, approximately −4 cm $H_2O$. If a patient takes a deeper breath, the intrapleural pressure will be more negative. A balloon or compliant reservoir and valve arrangement may allow such variations in pressure to pump matter or to assist pumping of matter. Where a device may benefit from circulating media for cells (e.g., in a cell reservoir), variations in pressure may be used to promote circulation or mixing of media to carry nutrients to cells and to remove waste products from the cells.

The switch 220 may be configured such that energy from a pulse generator 242, 244 is delivered to the cell reservoir 290 in a manner controlled by the processor 210. For example, the telemetry circuit 270 may receive a signal indicative of an intrinsic heart beat or one or more electrodes may sense cardiac electrical activity where energy is delivered to the cell reservoir based at least in part on such a signal or sensed activity. The switch 220 may be configured to allow for impedance or other measurements of the cell reservoir 290 and optionally the nutrient reservoir 292 and/or the pump 295. For example, impedance may indicate a change in cell density in the cell reservoir 290, a change in chemical composition or volume in the nutrient reservoir 292 and condition of the pump 295.

One or more of the physiological sensors 260 may be capable of sensing conditions of the cell reservoir 290, the nutrient reservoir 292 and/or matter passing through the pump 295.

While the device 200 includes particular features, various exemplary devices, systems, methods, etc., may use or be implemented using a different device or devices with more or less features. For example, one device may provide fluidics while another device provides information to the fluidics device. The device 200 may include features as associated with an insulin or other drug delivery device.

Figure 3:
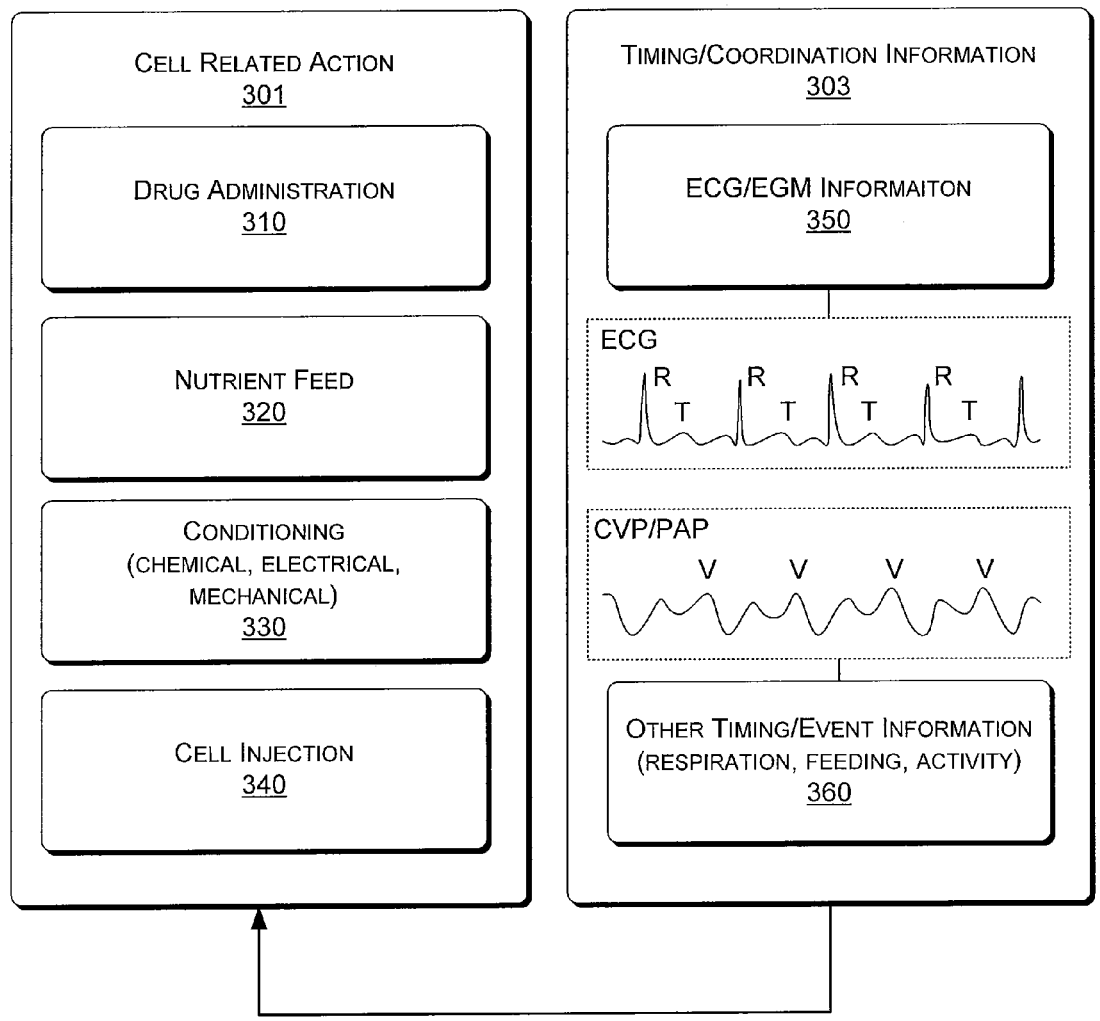
FIG. 3 is a diagram of various cell related actions and timing and/or coordination information for use in control of such actions.

FIG. 3 shows an exemplary scheme 300 where various cell related actions 301 coordinated with various event and/or condition information 303. The actions 301 include drug administration 310 (immune suppressant, growth factors, etc.), nutrient feed 320, conditioning 330 and cell injection 340. The information 303 includes ECG and/or EGM information 350 and other timing information 360 (e.g., as associated with various physiological cycles, whether intrinsic or therapy driven). As described herein, various exemplary devices, methods, systems, etc., perform cell related action based at least in part on event and/or condition information. For example, EGM information 350 may be used to time injection of cells to the heart 340 or respiration information 360 may be used to time delivery of nutrients to the heart 320. As examples, the ECG/EGM information 350 shows an ECG (a plot of electrical activity of the heart) while the other information 360 shows a plot of central venous pressure (CVP) or a pulmonary artery pressure (PAP) with A, C and V waves. A CVP/PAP A wave is associated with atrial contraction, a CVP/PAP C wave is associated with closure of the tricuspid valve and a CVP/PAP V wave is associated with ventricular contraction. The ECG or the CVP/PAP may be used for purposes of timing actions such as delivery of nutrients, injection of cells, etc. Further, a simultaneous ECG and CVP/PAP may be used for purposes of timing actions. In general, a CVP/PAP A wave follows an atrial event (e.g., intrinsic P wave or paced A wave) and a CVP/PAP V wave follows a ventricular event (e.g., intrinsic R wave or paced V wave).

Figure 4:
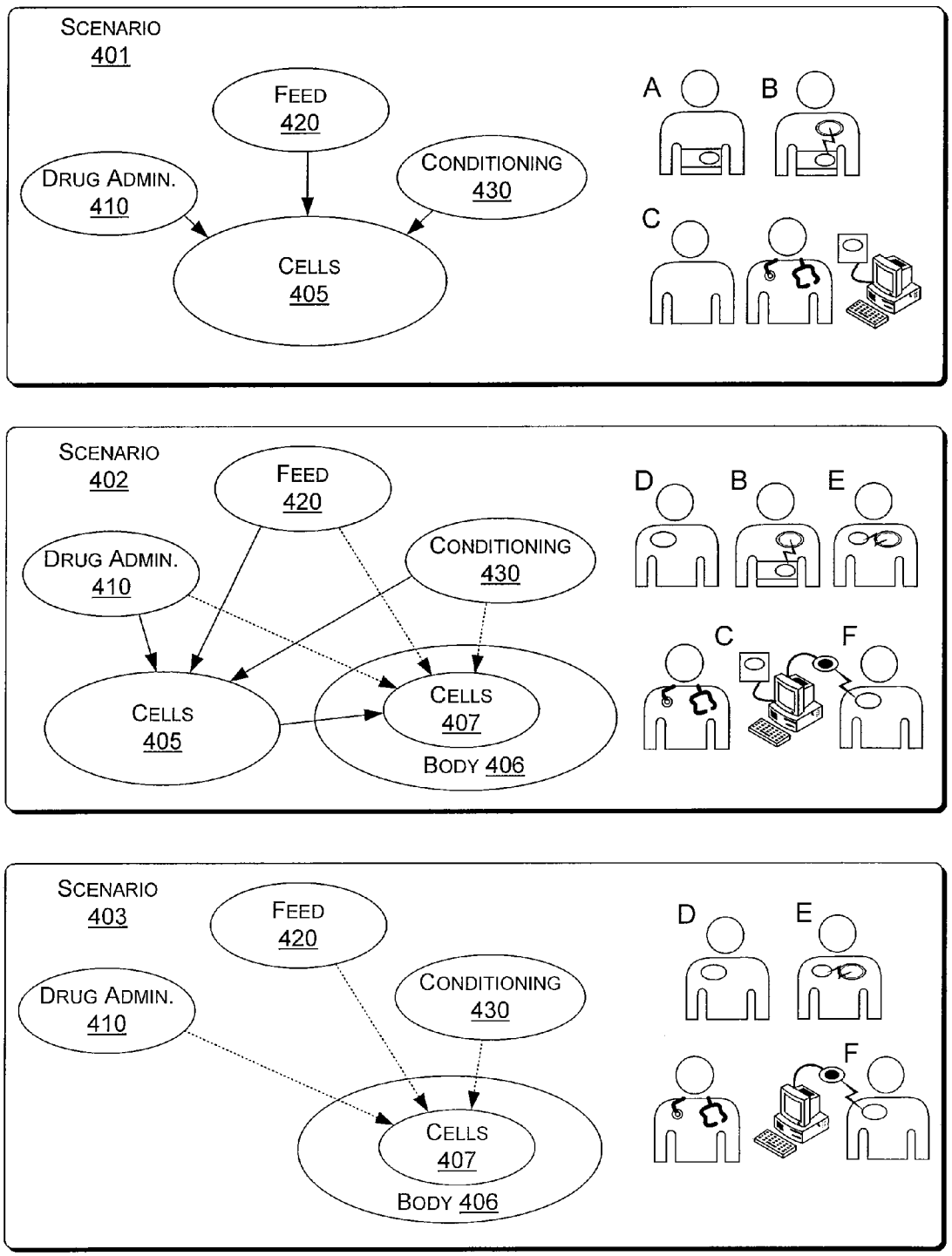
FIG. 4 is a diagram of three scenarios for cell related actions where cells may be in a reservoir in the body or external to the body or where cells may be in the body.

FIG. 4 shows various scenarios 401, 402, 403 for stem cell or related cell therapy and exemplary arrangements A, B, C, D, E and F for these therapies. The scenario 401 pertains to treating cells 405 that are external to the body of a patient. According to the scenario 401, actions such as drug administration 410, feeding 420 and conditioning 430 may occur. These actions may prepare the cells 405 for implantation in the body of a patient or for production of a particular chemical, which may be administered to a patient. For example, the cells 405 may produce a chemical that signals cell growth or growth of vascular structures. The chemical may be harvested from a cell reservoir and injected into a patient (e.g., myocardial injection, etc.) to thereby promote growth of myocytes, vascular structures, etc. While three exemplary arrangements (A, B and C) are shown as associated with scenario 401, other arrangements may be possible.

In arrangement A, a patient wears a device that includes a cell reservoir. The device may be fitted to a strap, a holster, etc., and may contact the body to help heat the cells. The device may sense patient physiology and response by administering a drug 410 to the cells 405, feeding 420 the cells 405 and/or conditioning 430 the cells 405. The device may include various features of the device 200 of FIG. 2. The cells 405 may be destined for injection into the heart or they may be used to produce chemicals for delivery to the heart.

In arrangement B, a patient wears an external device that includes a cell reservoir and the patient has an implanted device that may communicate information (e.g., data or a signal) to the external device. The implanted device may include features of the device 200 of FIG. 2 and may be capable of delivering a pacing or other stimulation therapy (e.g., cardiac, other muscle, nerve, etc.). As explained below, the implanted device may provide information regarding cardiac activity that can be used to administer a drug 410 to the cells 405, feed 420 the cells 405 and/or condition 430 the cells 405. The exemplary device 200 of FIG. 2 may be used to perform such actions.

In arrangement C, a clinician examines a patient and enters information to a controller that controls drug administration 410, feeding 420 and/or conditioning of the cells 405, which may be housed in a device such as an incubator. The clinician may have access to equipment such as an ECG unit for acquiring cardiac electrical information, which may then be used by the controller to control various actions related to the cells.

The scenario 402 pertains to treating cells 405 that are external to the body 406 and/or treating cells 407 that are in a reservoir in the body 406 or in the body 406. According to the scenario 402, actions such as drug administration 410, feeding 420 and conditioning 430 may occur. Various arrangements B, C, D, E and F are shown as being associated with scenario 402. Arrangements B and C are described above.

In arrangement D, a patient has an implanted device that may include a cell reservoir. The implanted device may treat cells in a cell reservoir or may treat cells that are not in a reservoir but rather located within a target region of the body such as the myocardium. The implanted device may include various features of the device 200 of FIG. 2.

In arrangement E, a patient has two implanted devices where uni-directional or bi-directional communication may occur. One device may be the implanted device described with respect to arrangement B while the other device may include a cell reservoir or features to treat implanted cells that are not in a reservoir. Thus, at least one of the devices in arrangement E is capable of delivering drugs 410, nutrients 420 and/or conditioning 430 cells.

In arrangement F, a clinician examines a patient and then uses a programmer to program an implanted device that can treat cells implanted in the patient whether in a reservoir or not. The programmer includes features for wireless communication with an implantable device capable of treating cells and optionally including a cell reservoir.

The scenario 403 pertains to treating cells 407 that are in a reservoir in the body 406 or in the body 406. According to the scenario 403, actions such as drug administration 410, feeding 420 and conditioning 430 may occur. Various arrangements D, E and F are shown as being associated with scenario 403, these arrangements are described above.

According to FIG. 4, various arrangements are possible for treating cells. An exemplary device, devices or a system may be capable of treating cells external to the body (scenario 401), capable of treating cells external to the body and internal to the body (scenario 402) or capable of treating cells internal to the body (scenario 403). An exemplary device, devices or a system may be capable of injecting one or more chemicals (e.g., drugs, etc., for purposes other than those directly related to treatment of implanted cells) or injecting cells into a patient, for example, as described with respect to FIG. 3 (cell injection 340). The device 200 of FIG. 2 may be suitably configured to operate according to any of the scenarios of FIG. 4.

An exemplary device may be capable of operating according to one or more of the scenarios 401, 402, 403. An exemplary device may be implantable, partially implantable, connectable to implantable or partially implantable components, or completely external, yet optionally configured to sense information or otherwise acquire information (e.g., ECG/EGM information 350 and/or other information 360). In general, an exemplary device acts at least in part on the basis of sensed and/or acquired information.

Figure 5:
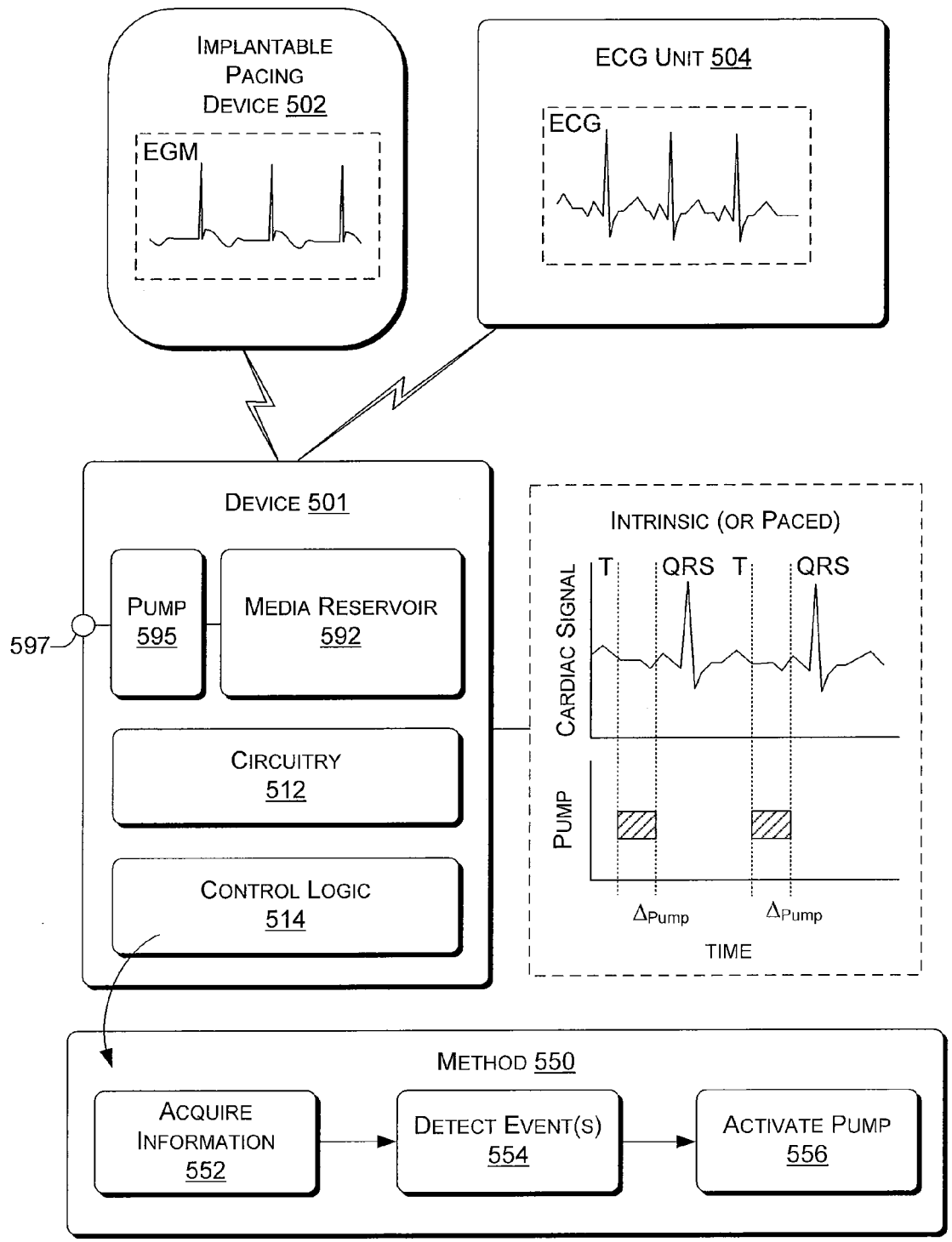
FIG. 5 is a diagram of an exemplary scenario for activating a pump to deliver matter based at least in part on ECG and/or EGM information.

FIG. 5 shows an exemplary scenario 500 for pumping media using ECG and/or EGM information. An exemplary device 501 includes circuitry 512, control logic 514, a media reservoir 592 and a pump 595 configured to pump media from the media reservoir 592 via a connector port 597. While the circuitry 512 of the device 501 may be capable of sensing cardiac electrical activity, in the example of FIG. 5, the circuitry 512 allows for acquisition of an EGM from an implantable pacing device 502 and/or for acquisition of an ECG from an ECG unit 504.

According to an exemplary method 550, the device 501 acquires information in an acquisition block 552, detects one or more events in a detection block 554 and activates the pump 595 in an activation block 556. A specific example detects end of a T wave to activate the pump and then deactivates the pump prior to a QRS complex. A pump activation time ($\Delta_{Pump}$) may depend on the amount of matter to deliver to a particular site or may depend on the heart being in a fairly relaxed state. Regarding the latter, the pump may operate more efficiently when pumping media into relaxed tissue as opposed to contracted tissue. Where cells are injected, such a method may increase retention of injected cells.

In general, dispersion, uptake, metabolism of pumped matter is of interest. Hence, pumped matter may include a contrast or tracking agent that allows for visualization or tracking the matter whether the matter includes cells, nutrient medium, drugs, etc. An exemplary method optionally delivers a contrast or tracking agent prior to delivery of other matter to understand how the latter delivered matter may disperse or be retained.

The exemplary method 550 may be used in conjunction with the method 110 of FIG. 1. For example, a conventional approach to injection of cells (e.g., stem cells, progenitor cells, etc.) may use ECG information and/or EGM information to time injection. An exemplary arrangement includes a syringe or injector that can sense cardiac electrical activity and use such sensed information for timing injection of cells. Referring to the exemplary lead 205 of FIG. 2, such a lead may be associated with an injector where the electrodes 207, 207' may be used to sense cardiac electrical activity. Injection of matter (cells or other matter) may occur according to a desired event or activity. Such an injector may repeatedly and incrementally inject matter, for example, after detection of an R wave, a sensed pacing stimulus, an evoked response, etc., optionally after a delay (e.g., 300 ms after detection of an R wave). Such an injector may allow for impedance measurement to determine whether the opening(s) are positioned appropriately (e.g., in tissue, in fluid, etc.). An injector may include control logic or circuitry that prohibits injection of matter based on impedance (e.g., as measured between catheter or lead electrodes, needle electrodes, etc.). The device 200 may operate as an injector that can sense cardiac electrical activity and/or measure impedance and inject or deliver matter based in part on such sensed or measured information.

An exemplary method may include acquiring cardiac electrical activity information, detecting a cardiac event based on the acquired cardiac electrical information and, based on the event, timing delivery of matter to the heart where the matter may be one or more of stem cells, progenitor cells, nutrients and drugs. In such a method, the cardiac event may be an R wave, a QRS complex, a T wave, a P wave, an evoked response, etc. The delivery of matter may occur during diastole and/or systole (e.g., ventricular diastole and/or ventricular systole). The delivery may deliver matter to the myocardium, an epicardial artery, etc.

Figure 6:
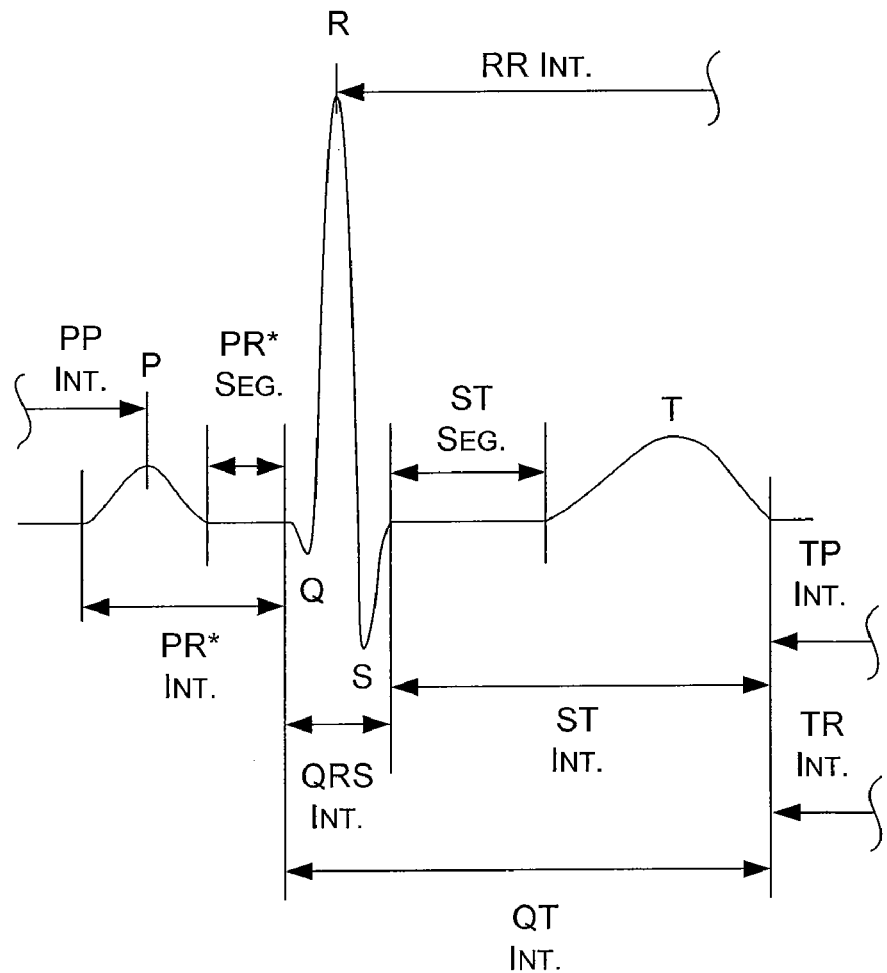
FIG. 6 is an ECG that illustrates various features associated with cardiac activity or cardiac condition.

While the scenario of FIG. 5 uses particular information in an ECG or an EGM, other information may be used depending on the function or purpose of an action. An explanation of various features of an ECG (or EGM) follows with respect to FIG. 6, which shows an ECG 600 for one cardiac cycle. The ECG 600 includes various peaks, segments and intervals, some of which have been mentioned above. While one ECG is shown in FIG. 6, depending on specific features of an ECG acquisition system, multiple plots may be acquired. For example, a multiple lead ECG acquisition system can acquire multiple plots for a single cardiac cycle. In general, each plot is associated with a different lead configuration and hence shapes and timings of the various peaks, segments and intervals may vary from plot to plot.

Most ECG acquisition systems rely on multiple leads. For example, one fairly standard multiple lead ECG acquisition system relies on 7 leads while another relies on 12 leads. The standard 7 lead system includes leads labeled I, II, III, aVR, aVL and aVF while the standard 12 lead system also includes leads labeled V1 through V6. The labels correspond to surface positions with respect to the body.

Given this brief background on multiple lead ECG acquisition systems, the various components of the ECG 600 are now described. In general, depending on detection technique, etc., a "wave" may be assigned a time associated with the beginning of the wave, the end of the wave, a peak amplitude of the wave, etc. Also, in some instances, an R wave may be assigned a time associated with the beginning of the QRS complex. Regardless of the convention used, consistency in detection allows for more accurate assessment of patient condition and/or control of therapeutic actions (e.g., actions related to cells, etc.).

Various peaks are labeled in FIG. 6. The peak labeled "P" corresponds to a P wave caused by depolarization of the atrial myocardium. A normal P wave usually has a width of less than about 110 ms.

An interval that is measured from the beginning of a P wave to the beginning of the QRS complex, is referred to as the PR interval, which represents atrial depolarization plus an AV nodal delay. The PR interval is typically in a range from about 120 ms to about 200 ms. Where AV conduction is impaired, the PR interval is lengthened (e.g., first-degree AV block). The PR interval includes the PR segment, which begins at the end of the P wave and ends with the onset of the QRS complex. Elevation of the PR segment may indicate disease such as atrial infarction or pericarditis. Depression of the PR segment may occur if a large atrial repolarization wave exists.

While labeled as individual peaks in the ECG 600, the QRS complex represents depolarization of the ventricular myocardium. While depolarization of the AV node, His bundle, bundle branches, and Purkinje fibers also occurs, the electrical signals emerging from these cardiac structures are typically too small in amplitude to be detected by electrodes on the body surface. A "normal" QRS complex will typically have a width ranging from about 70 ms to about 110 ms.

Various conditions may be determined on the basis of the R wave or R wave progression in a multi-lead system. For example, an early R wave in leads V1 and V2 having a magnitude as large as those in the next several leads (e.g., V3, V4, V5) can reflect posterior infarction, lateral MI, right ventricular hypertrophy (RVH), or septal hypertrophy. Also consider a large magnitude R wave in V1, which may indicate RVH, posterior MI, or Wolff-Parkinson-White (W-P-W). A poor R wave progression, e.g., R waves that do not begin to dominate the QRS complex until V5 or V6, may represent infarction or injury of the anterior LV.

Small magnitude R waves in the right precordial leads may be due to left ventricular hypertrophy (LVH), left anterior fascicular block (LAFB), COPD, or MI. LVH causes loss of R wave magnitude from V1-V3 without MI. Loss of R magnitude between V1-V2 or V2-V3 in the absence of LVH suggests anterior MI.

With respect to the Q Wave, not all leads may record a Q wave. Normal Q waves typically represent septal depolarization. Q waves should be distinguished from pathologic Q waves that can indicate myocardial infarction. A "normal" Q wave is usually present in leads I, aVL, V5, and V6 (left lateral leads) only and has a width of about 4 ms. A small Q wave may be evidenced in aVF and V5 leads. Lack of a Q wave may indicate septal fibrosis; whereas, a large Q wave (magnitude), may indicate myocardial damage, as large, diagnostic Q waves represent altered electrical activity in the myocardium due to transmural myocardial damage. Note however that a diagnostic Q wave in V1, aVL, or III may be present without indicating myocardial damage.

An ST segment commences at the "J point" (end of the QRS complex) and ends at the onset of the T wave. The ST segment represents the duration for which ventricular cells are in the plateau phase (phase 2) of the action potential (where there is no current flow and thus little, if any, transmembrane gradient). QRS complex width and ST segment also represent the duration of the ventricular absolute refractory period, where the ventricles will generally not respond to stimulation. The ST segment should be isoelectric with a smooth contour. In instances where it is not isoelectric, the ST segment may be characterized as ST depression or ST elevation.

The QT Interval is a measure of the refractory period during which the myocardium would not respond to a second impulse and it is typically measured from the beginning of the QRS complex to the end of the T wave. Some consider leads V2 or V3 as providing the most accurate QT interval. A basic rule indicates that the QT interval should be roughly less than half the preceding RR interval. QT interval normally varies with heart rate. QT interval may also be affected by width of the QRS complex such as a bundle branch block, which increases the QT interval. Thus, ST interval may be considered to compensate for a wide QRS complex.

A measure referred to as QT dispersion is determined on the basis of QT intervals from various (or all) ECG leads where the shortest QT interval ($QT_{Min}$) is subtracted from the longest QT interval ($QT_{Max}$). A substantial difference between these two QT intervals may indicate that heterogeneous refractoriness exists and that the patient may be at higher risk of cardiac death from development of ventricular tachycardia/fibrillation, especially from any proarrhythmic effects of antiarrhythmic drugs.

JT intervals may be measured to reflect repolarization. The JT interval is sometimes used to measure the refractory period in patients treated with a Na+ channel blocker antiarrhythmic drugs (e.g., Quinidine, Pronestyl, and other class I agents), which slow depolarization and prolong the QRS complex.

The T wave represents repolarization of the ventricles and the earliest the ventricles can respond to another stimulus usually coincides with the apex of the T wave. Shortly after the T wave begins the ventricles start to relax (ventricular diastole). Contractile fibers in both atria and ventricles are relaxed for about 200 ms to about 400 ms, typically shorter for higher heart rate. In the ECG 600, the heart is typically relaxed (e.g., "relaxation period") during the TP interval and the ventricles relaxed during the TR interval.

ST deviation and T wave abnormalities are seen with conditions other than myocardial ischemia such as a wide QRS complex or secondary to effects of medications. It is possible to have both primary and secondary changes (e.g., bundle branch block plus ischemia). In this case, the ST segment may appear to normalize because both ST depression and elevation are occurring simultaneously.

Various exemplary techniques described herein deliver matter when the ventricles are relaxed. Referring again to the scenario 500 of FIG. 5, activation of a pump occurs to deliver media during a relaxed period, as indicated by an ECG or an EGM. Contraction and relaxation of the heart are associated with movement of calcium from the extracellular space and from the stores in the sarcoplastic reticulum. Contraction occurs when an action potential causes the influx of calcium and relaxation occurs when the depolarization ceases and calcium is removed from the sarcomere. An increase in intracellular calcium interacts with the actin binding site so that cross-bridges can attach and thereby allow for contraction to take place. In absence of calcium, binding sites are covered and the fibers relaxed, i.e., no significant overlap of actin and myosin exists.

Contraction and relaxation require energy derived from ATP. For an ischemic region, availability of ATP may be limited and the ability to remove calcium impaired, resulting in continued coupling of actin/myosin cross-bridges. Thus, muscle in an ischemic region may become stiff and less compliant. Various techniques may deliver matter to a boundary of an ischemic region, which may be more compliant and more capable of responding to therapy. Further, particular therapies aim to repair ischemic regions or affect tissue at the boundary of an ischemic region. Such techniques may rely on ECG, EGM or other information to more effectively deliver a therapy.

Figure 7:
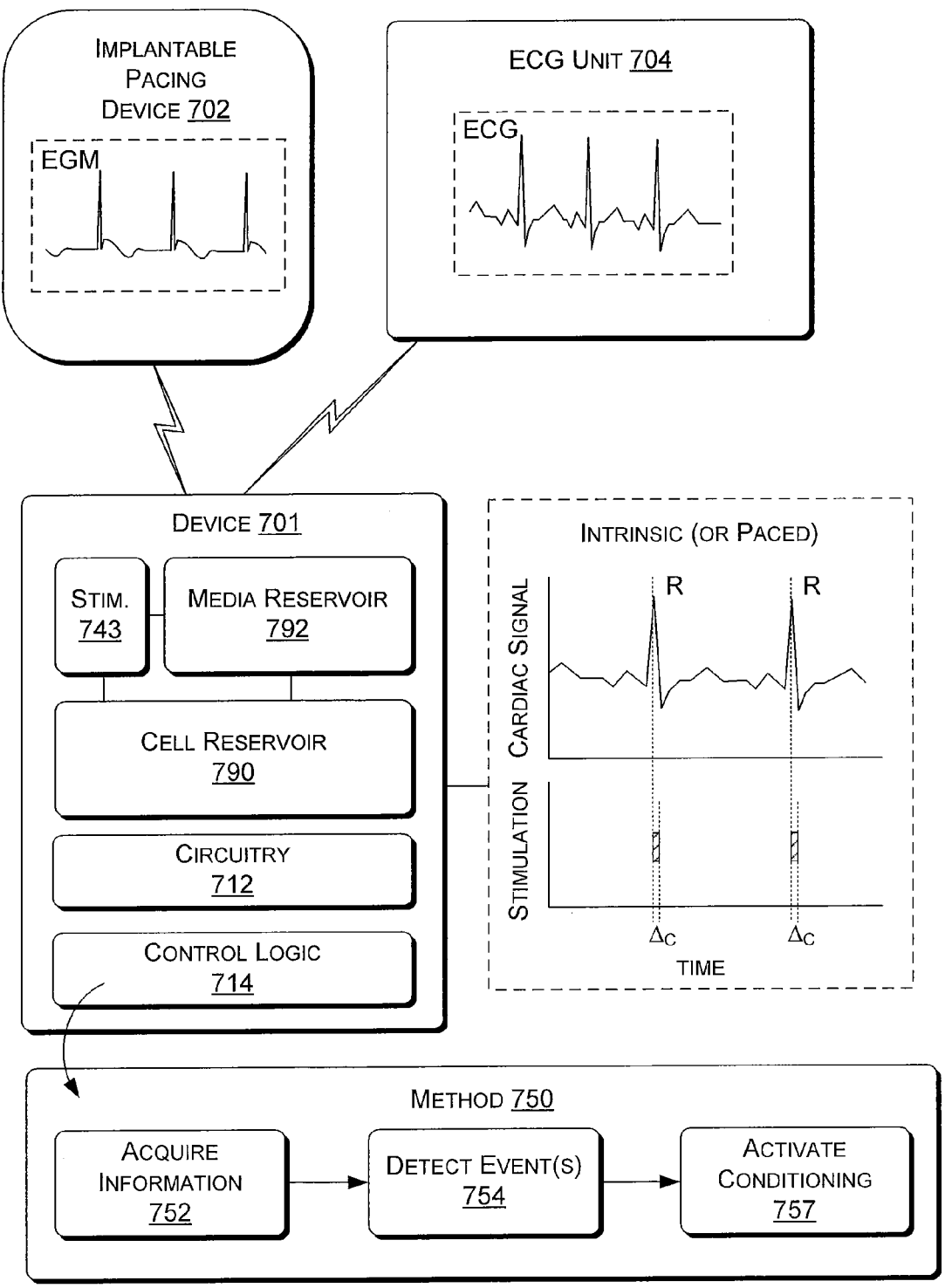
FIG. 7 is a diagram of an exemplary scenario for conditioning cells based at least in part on ECG and/or EGM information.

With respect to conditioning cells, EGM/ECG information or other information may be used for timing delivery of electrical energy, mechanical energy, a chemical, etc. For example, FIG. 7 shows an exemplary scenario 700 for conditioning cells using ECG/EGM information. The scenario 700 uses an exemplary device 701 that includes circuitry 712, control logic 714, stimulation circuitry 743, a cell reservoir 790 and a media reservoir 792. While the circuitry 712 of the device 701 may be capable of sensing cardiac electrical activity, in the example of FIG. 7, the circuitry 712 allows for acquisition of an EGM from an implantable pacing device 702 and/or for acquisition of an ECG from an ECG unit 704.

According to an exemplary method 750, the device 701 acquires information in an acquisition block 752, detects one or more events in a detection block 754 and activates the stimulation circuitry 743 in an activation block 757 to condition cells in the cell reservoir 790. A specific example detects an R wave to activate the conditioning and then deactivates the conditioning after expiration of an activation time ($\Delta_C$), which may depend on properties of cells, cell density, etc.

As already mentioned, an exemplary device may be implantable, partially implantable, connectable to implantable or partially implantable components, or completely external, yet optionally configured to sense information or otherwise acquire information (e.g., ECG/EGM information 350 and/or other information 360). Thus, the device 701 may be an implantable pacing device capable of delivering pacing or other cardiac stimulation therapies (e.g., defibrillation, etc.). In such an example, conditioning of cells in a reservoir may occur in a coordinated manner with delivery of stimulation energy to a patient's heart. For example, if a pacing therapy calls for delivery of stimulation energy to the right ventricle at a rate of 72 beats per minute, then the device 701 may condition cells in the cell reservoir 790 at the same rate or a rate based at least in part on the pacing therapy rate. Further, where the device 701 includes control logic for adjusting pacing rate responsive to patient activity, then delivery of energy to condition cells in the cell reservoir 790 may also be adjusted.

According to the exemplary method 700, a goal may be to minimize risk of paroxysmal arrhythmia due to the cells, for example, once implanted into the myocardium. The exemplary device 701 may therefore provide stem cell therapy to minimize the paroxysmal arrhythmia by electrical pacing. If such treated cells are implanted, then further treatment may occur. Such treatment may include use of electrical pacing where pacing optionally occurs at an energy level less than the capture threshold for neighboring myocardium and/or where deliver of such energy occurs during a refractory period of the neighboring myocardium. Hence, the conditioning may use EGM and/or ECG information to determine a refractory period of neighboring myocardium and then use this information to activate conditioning of implanted cells.

Where a patient is fitted with an implantable device for cardiac pacing therapy, an exemplary method may include calling for delivery of an extra-stimulus. For example, such a method may include calling for delivery of cardiac pacing pulses at a pre-determined rate and calling for delivery of one or more cell conditioning pulses. In general, the delivery of the one or more cell conditioning pulses occurs at a time other than that of a cardiac pacing pulse. Further, any or all of the one or more cell conditioning pulses may have an energy insufficient to cause cardiac capture.

An exemplary method may call for delivery of the one or more cell conditioning pulses at a pre-determined frequency or at a frequency that depends at least in part on acquire cardiac information, whether acquired via sensing by an implantable device that implements the method or by an external device that transmits the information to an implantable device that implements the method. The frequency may be once per cardiac cycle or at a greater or lesser frequency.

An exemplary method may call for delivery of cell conditioning pulses to implanted cells, cells destined for implantation and/or cells producing a therapeutic agent (e.g., drug, etc.). With respect to implanted cells, such cells may be implanted in the myocardium.

As already mentioned, an exemplary method may delivery energy to cells implanted in the heart at an energy level less than a capture threshold of surrounding myocardial tissue or, more generally, at a level insufficient to cause cardiac capture. Such a method may include determining a cardiac capture threshold prior to calling for delivery of one or more cell conditioning pulses. Further, such a method may include determining an energy for any or all conditioning pulses based at least in part on a cardiac capture threshold. An exemplary method may call for delivery of one or more cell conditioning pulses during a myocardial, non-refractory period and/or during a myocardial, refractory period.

Figure 8:
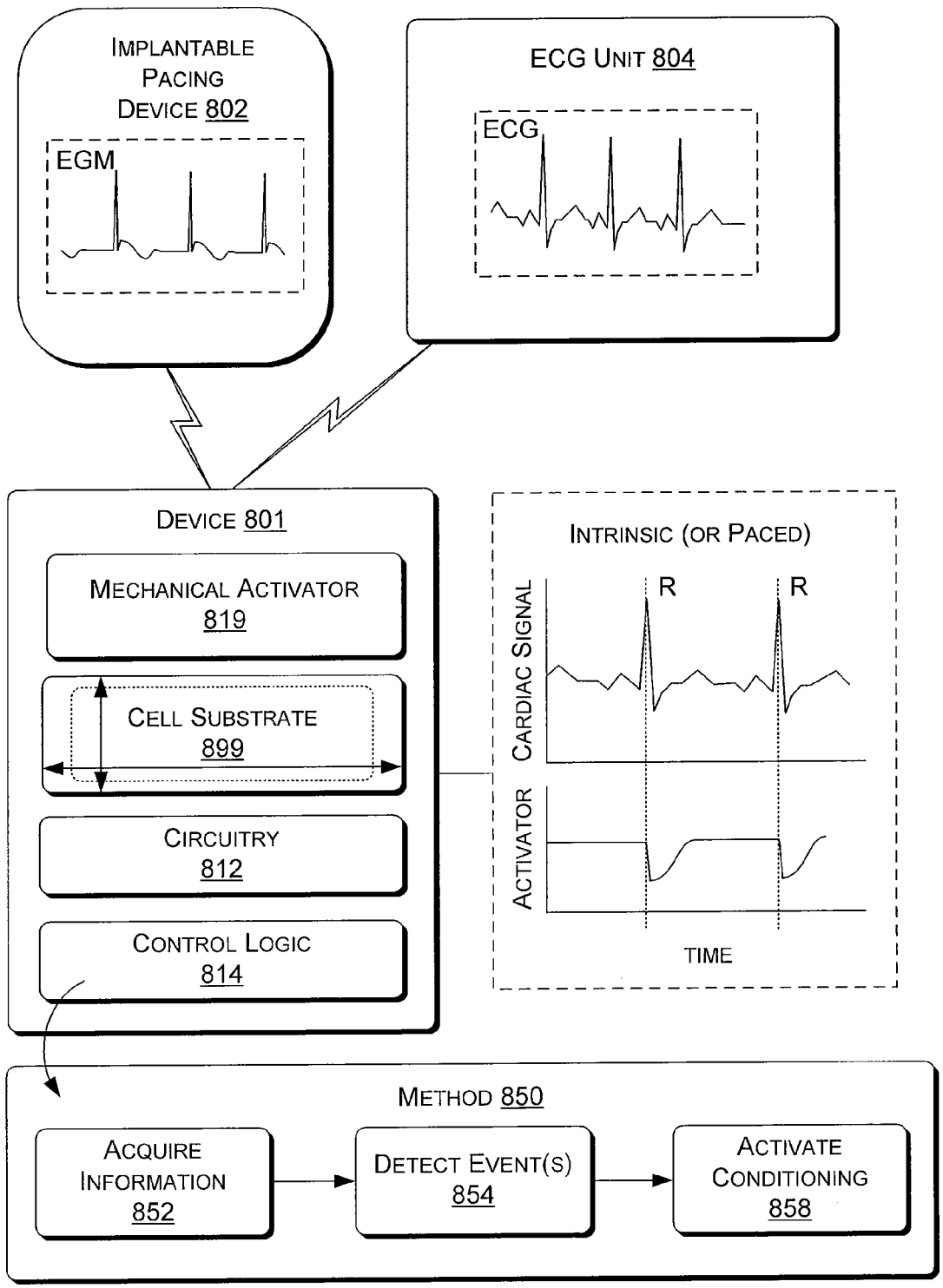
FIG. 8 is a diagram of an exemplary scenario for mechanically conditioning cells based at least in part on ECG and/or EGM information.

As already mentioned, cells may be conditioned in any of a variety of manners. FIG. 8 shows an exemplary scenario 800 where mechanical conditioning of cells occurs based at least in part on ECG information or EGM information. The scenario 800 uses an exemplary device 801 that includes circuitry 812, control logic 814, a mechanical activator 819 and a cell substrate 899. The cell substrate 899 generally provides for anchoring of cells, directional alignment of cells, scaffolding of cells into macrostructures, etc. The mechanical activator 819 may cause the cell substrate 899 to bend, stretch, shear, vibrate, etc., in a manner that promotes beneficial cell behavior. For example, a bendable polymer substrate may mimic actin-myosin dimension changes of myocardial tissue. The bendable substrate may be operably connected to a mechanical activator that deforms responsive to applied current or voltage (e.g., dissimilar metals circuit, piezoelectric circuit, etc.). The cell substrate 899 may be a sponge or other porous structure that can serve as a support for cells. Thus, the mechanical activator 819 may be configured to deform such a structure to thereby condition the cells and optionally increase transport of nutrients and/or waste products.

While the circuitry 812 of the device 801 may be capable of sensing cardiac electrical activity or mechanical activity, in the example of FIG. 8, the circuitry 812 allows for acquisition of an EGM from an implantable pacing device 802 and/or for acquisition of an ECG from an ECG unit 804.

According to an exemplary method 850, the device 801 acquires information in an acquisition block 852, detects one or more events in a detection block 854 and activates the mechanical activator 819 in an activation block 858 to condition cells associated with the cell substrate 899. A specific example detects an R wave to cause the mechanical activator 819 to mechanically deform or move the cell substrate 899. A wave form for activation may be adjusted based on cell properties, cell density, etc. In general, the conditioning promotes cell properties or behavior for production of chemicals and/or for implant of such cells.

The device 801 may be external to the body. For example, the device 801 may be wearable such that it is in contact with the body to receive heat from the body. The device 801 may include circuitry to acquire ECG information or other physiological information for use in conditioning cells. The device 801 may receive a signal from an implantable device (e.g., the device 802) when in close proximity to the implantable device. Such a signal may simply indicate a pacing rate or detection of an R wave or other cardiac event, which may, in turn, be used for conditioning cells associated with the cell substrate 899.

Figure 9:
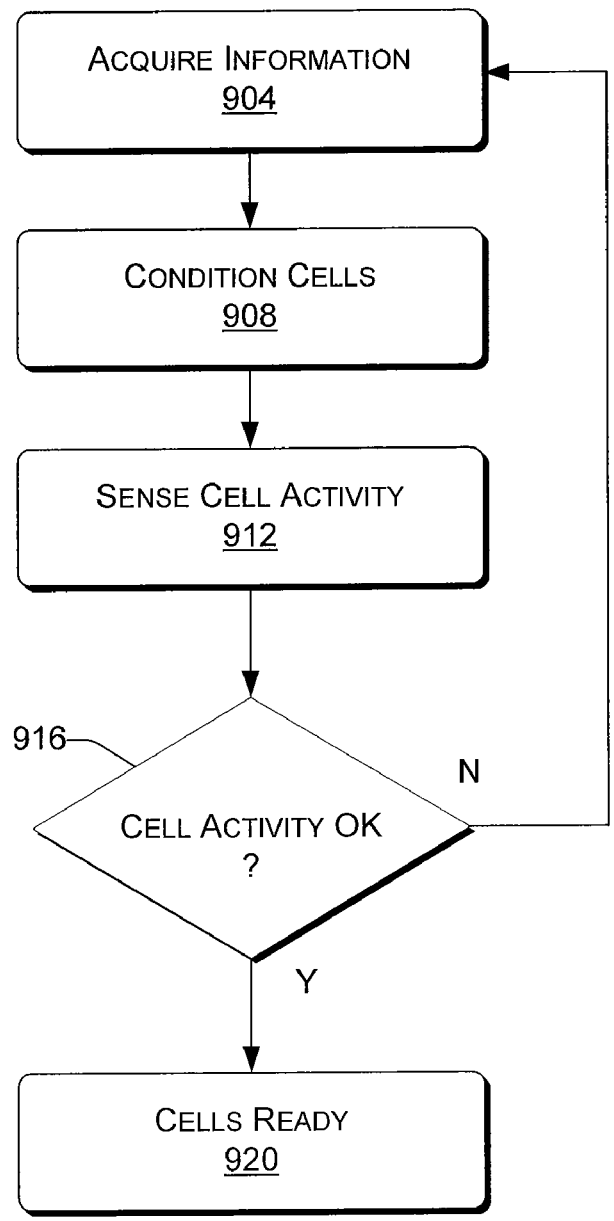
FIG. 9 is a diagram of an exemplary method for conditioning cells and deciding whether cells have been adequately conditioned.

As already mentioned, conditioning may promote desirable cell properties, behavior, etc. FIG. 9 shows an exemplary method 900 for conditioning cells and deciding if such conditioning has promoted desirable cell activity. The method 900 commences in an acquisition block 904 that acquires information such as ECG, EGM or other information. A conditioning block 908 uses the acquired information to condition cells, for example, via administration of a drug, delivery of electrical energy, mechanical deformation, etc. In the example of FIG. 9, the conditioning aims to promote certain desirable cell activity that may be sensed by a sense block 912. The sense block 912 may sense electrical activity of the cells, properties of the cells, behavior of the cells responsive to conditioning, etc. The sensing may use sensors or circuitry associated with a device (e.g., connected to a cell reservoir, a flow path, etc.) or may use a sample from a device for analysis by another device. For example, a port such as ports 291, 293, 296 of the device 200 of FIG. 2 may be used to acquire a sample from a cell reservoir, a nutrient reservoir, a flow path, etc.

After sensing, the method 900 enters a decision block 916 that decides if the sensed cell activity is OK, i.e., indicative of desirable activity. If the decision block 916 decides that the activity is OK, then the method 900 continues in a cell ready block 920, which indicates that the cells are ready for implantation, production of desirable chemicals, etc. (see, e.g., the methods 110, 120 of FIG. 1 and various other methods). If the decision block 916 decides that the cells are not ready, then the method 900 may continue at the acquisition block 904 for further conditioning or other action may occur (e.g., administration of nutrients, termination of cells, etc.).

With respect to sensed cell activity, conditioning may aim to achieve a certain level of cell contractility. Thus, sensing may occur during delivery of a stimulus where the sensing can determine how the cells contracted. Such sensing may monitor fluid composition or mechanical action (e.g., force, shear, motion, etc.). A piezoelectric sensor may be used to measure force exerted by cells (e.g., a layer of cells or other multi-cellular structure).

Conditioning may aim to control growth and alignment of cells. In such an example, the sensing may sense impedance or other electrical properties that vary with respect to cell alignment. For example, if the cells are not aligned, then a high resistance to current may exist along an axis of a cell reservoir; whereas, aligned cells may exhibit less resistance to current along the axis. In another example, resistance to current may be measured along more than one axis. Where a low resistance occurs along one axis and a high resistance occurs along another axis then the cells may be considered aligned along the low resistance axis.

The exemplary method 900 may apply to cells already injected into the body (e.g., into the myocardium) such as in the method 110 of FIG. 1. In such an example, the cell ready block 920 may simply indicate that no further conditioning is required for the already injected cells. Where cells are already injected, the conditioning may include generation of an electro-magnetic field at or near the site of injection or the resting site of the cells (e.g., as determined using imaging or other techniques). As already mentioned, the lead 205 includes electrodes 207, 207' capable of generating an electro-magnetic field. Such a field may aim to control the effect of intrinsic or paced activity on the injected cells by enhancing, diminishing or otherwise altering the local environment. For example, as the outer or lateral wall of the left ventricle experiences significant stress, delivery of stimulation energy or generation of a field in a region where cells have been injected may promote growth, retention of cells, etc. Where delivery of electrical energy occurs to or near a site where cells have been injected, delivery of electrical energy may occur during a refractory period of the heart to avoid capture of the heart or other undesirable effects. Alternatively, or in addition to, amplitude or duration of any electrical energy delivered may be adjusted to be less than a capture threshold of the heart.

Figure 10:
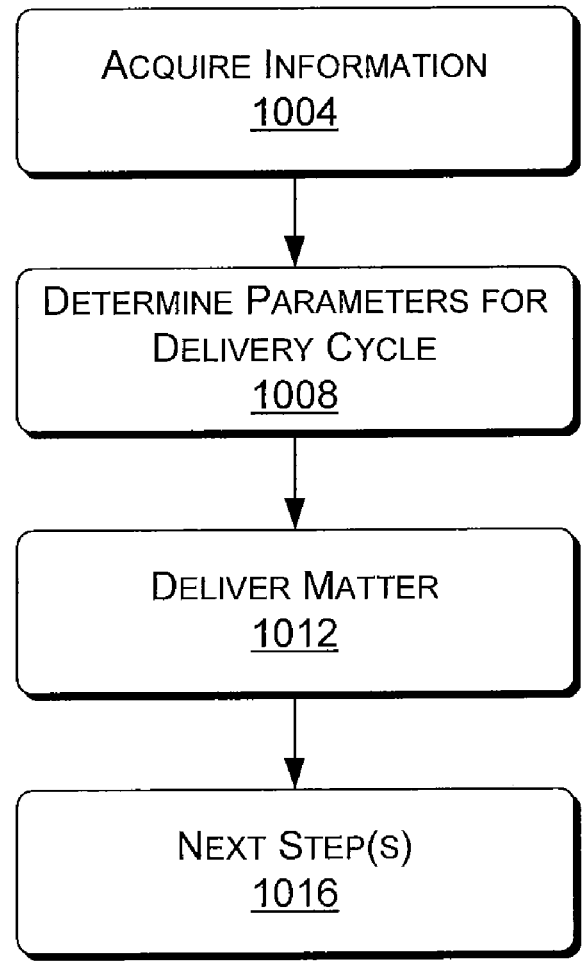
FIG. 10 is a diagram of an exemplary method for delivering matter based at least in part on physiological information.

FIG. 10 shows an exemplary method 1000 for delivery of matter such as nutrients, cells, drugs, etc. The method 1000 commences in an acquisition block 1004 that acquires information. The information may include information related to patient physiology such as electrical activity of the heart and may include information related to a therapy, for example, a dose of a drug or a number of cells to inject.

The method 1000 continues in a determination block 1008 that determines appropriate parameter values for a delivery cycle to deliver matter. For example, the delivery cycle may call for delivery of a certain number of cells using a solution having a certain cell density. The determination block 1008 may determine a number of individual injections required for a delivery cycle to achieve the number of cells. Further, each injection may be timed to a cardiac cycle where timing of an individual injection occurs during a relaxation period of the heart (e.g., based on T wave, etc.). The determination block 1008 may consider retention of matter at a particular delivery site, diffusion of matter, concentration of matter, etc., in an effort to optimize delivery and effectiveness of the delivered matter.

Once the parameter values have been determined, the method 1000 delivers the matter via a delivery block 1012. The delivery block 1012 may operate to deliver matter over a certain number of cardiac cycles where delivery of matter may occur every cardiac cycle or according to some other basis (e.g., every 10th cardiac cycle, etc.). After delivery of the matter, the method 1000 continues in a next step(s) block 1016, which may take any of a variety of actions such as returning to the acquisition block 1004 to acquire information that may help evaluate the effectiveness of the delivered matter.

The exemplary method 1000 may include acquiring cardiac electrical activity information, detecting a T wave and, based on the detecting, calling for delivery of matter to the heart wherein the matter comprises at least one member selected from a group consisting of stem cells, progenitor cells, nutrients and drugs. The detection of the T wave may allow for delivery during a relaxation period of the heart to improve effectiveness of the delivery.

Figure 11:
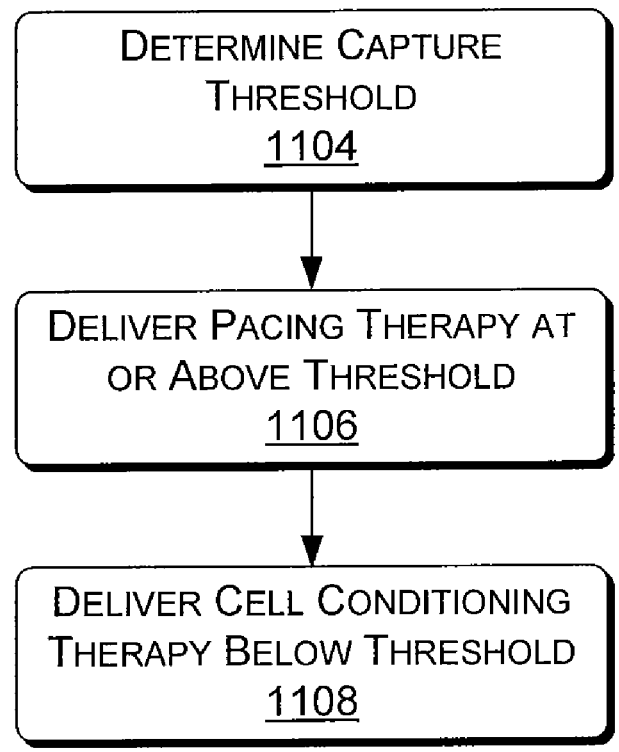
FIG. 11 is a diagram of an exemplary method for delivering cardiac pacing therapy and cell conditioning, based at least in part on a capture threshold.

FIG. 11 shows an exemplary method 1100 that includes delivery of a cardiac pacing therapy and a cell conditioning therapy based at least in part on a cardiac capture threshold. The method 1100 commences in a determination block 1104 that determines a cardiac capture threshold, for example, using a conventional capture detection technique (e.g., search algorithm that uses various stimulation energies or timings, etc.). In a delivery block 1106, the method 1100 delivers pacing therapy at or above the determined cardiac capture threshold. Another delivery block 1108 of the method 1100 delivers cell conditioning therapy (e.g., electrical stimulation of cells) below the determined cardiac capture threshold. The cells to be conditioned may be implanted in the myocardium or in a reservoir, which may be located proximate to the myocardium. In such a manner, cell conditioning avoids inadvertent capture of the myocardium.

Various exemplary techniques may aim to control (enhance or reduce) nerve sprouting and hyperinnervation. For example, both radiofrequency ablation and stem cell implantation have been reported to induce nerve sprouting and heterogenous sympathetic hyperinnervation. Techniques may aim to reduce such nerve phenomena (and/or the coexistence of adjacent denervated and hyperinnervated areas), which, in turn, may reduce risk of arrhythmia.

As already mentioned, various techniques aim to reduce risk of arrhythmia (less arrhythmogenesis). In various examples, a cardiac pacing device may promote cardiac cell alignment and post-injection cell function after injecting stem cells in the myocardium as remodeled cardiac cells are known to align better structurally and exhibit less arrhythmogenesis.

Various exemplary implantable devices include a reservoir for one or more stem cell based progenitors and control logic to control injection of the stem cell progenitors to a particular portion of the body (e.g., the heart) and/or to control pacing at an injection site to promote cell adaptation and cell growth. Such a device may include an indented funnel-like injection port for adding medication or other matter after the device has been implanted. With respect to delivery of matter, such delivery may occur according to a rate controlled by an implantable device and/or an external device.

An exemplary system may include a pacing lead that also acts as a syringe needle for delivery of cells or other matter. An implantable device may include multiple leads where the leads are configured to delivery energy and/or matter to the myocardium or associated vessel. In such a system, a pulse may be delivered via one lead at one time and a pulse delivered via another lead at another time. Such times may be associated with systole or diastole and more specifically may be during a refractory period or non-refractory period. Each of the pulses may be less than a capture threshold or greater than a capture threshold.

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method comprising:
   acquiring cardiac electrical activity information using at least two electrodes positioned on a surface of a distal end of a lead implanted adjacent cardiac tissue, wherein the lead includes at least one opening through the surface on which the at least two electrodes are positioned, wherein the opening is positioned between the at least two electrodes;
   detecting cardiac events within the information including T waves, QRS complexes and P waves;
   measuring impedance between two of the electrodes; and
   when the impedance measurement indicates the at least one opening is in cardiac tissue, delivering matter to the heart through the at least one opening through the surface on which the at least two electrodes are positioned, wherein the opening is positioned between the at least two electrodes, wherein delivery occurs at a time between a detected T wave and its immediately subsequent QRS complex, and
   when the impedance measurement indicates the at least one opening is not in cardiac tissue, prohibiting the delivery of matter to the heart through the at least one opening; wherein the measuring and delivering occur repeatedly and incrementally after the detection of the cardiac events.

2. The method of claim 1 wherein the acquiring comprises acquiring an EGM.

3. The method of claim 2 wherein the acquiring comprises acquiring the EGM using an implantable device.

4. The method of claim 1 wherein the matter comprises at least one member selected from a group consisting of stem cells, progenitor cells, nutrients and drugs.

5. The method of claim 1 further comprising using the measured impedance to determine if matter delivered is in contact with the electrodes.

6. The method of claim 1 further comprising using the measured impedance to determine if fouling has occurred at the at least one opening.

7. The method of claim 1 further comprising generating an electro-magnetic field using the at least two electrodes.

8. The method of claim 1 wherein the at least one opening is defined by a prong extending outward from the surface on which the at least two electrodes are positioned, wherein the prong is positioned between the at least two electrodes.

9. The method of claim 1 wherein the lead includes a plurality of openings, each defined by a prong extending outward from the surface on which the at least two electrodes are positioned, wherein the prong is positioned between the at least two electrodes and at least two of the prongs have different lengths.

10. The method of claim 1 wherein the distal end of the lead comprises a screw structure defining the surface on which the at least two electrodes are positioned and through which the opening extends.

11. The method of claim 1 wherein the matter comprises cells and further comprising delivering one or more cell conditioning pulses to the cells delivered to the heart.

12. The method of claim 11 wherein the one or more cell conditioning pulses comprise an energy insufficient to capture the heart.

13. A method comprising:
    acquiring cardiac electrical activity information using at least two electrodes positioned on a surface of a distal end of a lead implanted adjacent cardiac tissue, wherein the lead includes at least one opening through the surface on which the at least two electrodes are positioned, wherein the opening is positioned between the at least two electrodes;
    detecting cardiac events within the information including T waves, QRS complexes and P waves;
    measuring impedance between two of the electrodes; and
    when the impedance measurement indicates the at least one opening is in cardiac tissue, delivering matter to the heart through the at least one opening through the surface on which the at least two electrodes are positioned, wherein the opening is positioned between the at least two electrodes, wherein delivery occurs at a time between a detected T wave and its immediately subsequent P wave; and
    when the impedance measurement indicates the at least one opening is not in cardiac tissue, prohibiting the delivery of matter to the heart through the at least one opening; wherein the measuring and delivering occur repeatedly and incrementally after the detection of the cardiac events.

14. The method of claim 13 wherein the matter comprises at least one member selected from a group consisting of stem cells, progenitor cells, nutrients and drugs.

* * * * *